United States Patent [19]

Aiyar et al.

[11] Patent Number: 5,797,923
[45] Date of Patent: Aug. 25, 1998

[54] ELECTRODE DELIVERY INSTRUMENT

[76] Inventors: Harish Aiyar, 12851 Cedar Rd., Cleveland Heights, Ohio 44118; J. Thomas Mortimer, 13753 County Line Rd., Chagrin Falls, Ohio 44022

[21] Appl. No.: 854,564

[22] Filed: May 12, 1997

[51] Int. Cl.$^6$ ............................................. A61B 17/00
[52] U.S. Cl. ................................. 606/129; 606/167
[58] Field of Search ........................... 606/106, 108, 606/129, 167, 170, 222, 223

[56] References Cited

U.S. PATENT DOCUMENTS

| | | | |
|---|---|---|---|
| 5,431,671 | 7/1995 | Nallakrishnan | 606/167 |
| 5,586,986 | 12/1996 | Hinchliffe | 606/147 |
| 5,586,990 | 12/1996 | Hahnen et al. | 606/170 |

Primary Examiner—Michael Buiz
Assistant Examiner—David O. Reip
Attorney, Agent, or Firm—Jerrold J. Litzinger

[57] ABSTRACT

A surgical instrument for implanting electrodes within the muscular tissue of the diaphragm of a mammal through the abdomen. The instrument has an elongate frame with a first handle at one end. A needle for carrying the electrode is rotatably mounted on the other end of the instrument. The needle is located within a channel below the outer surface of the frame when the instrument is not in use. A second handle is connected to the needle by an actuating mechanism such that when the instrument is operated by moving the second handle toward the first handle, the needle rotates out from the frame to enable the instrument to accurately implant the electrode.

13 Claims, 4 Drawing Sheets

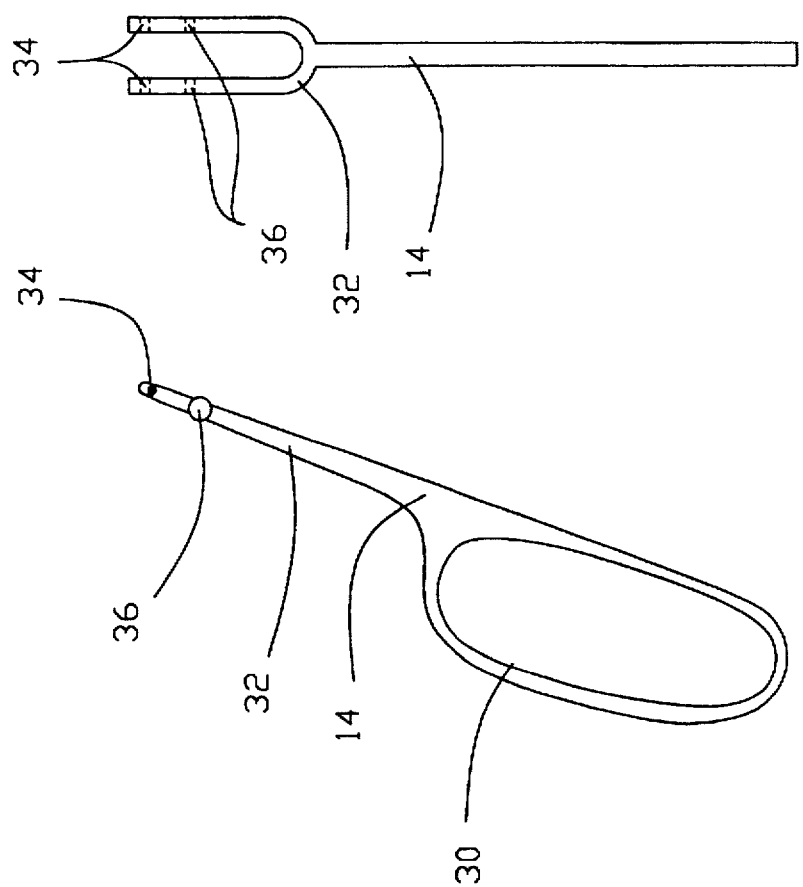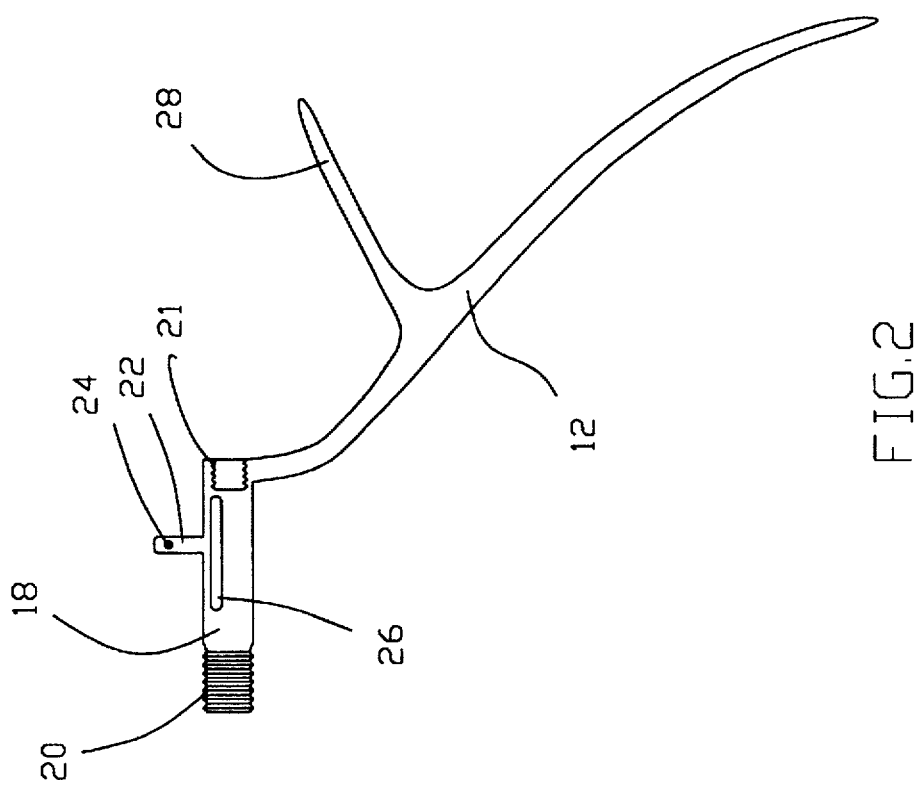

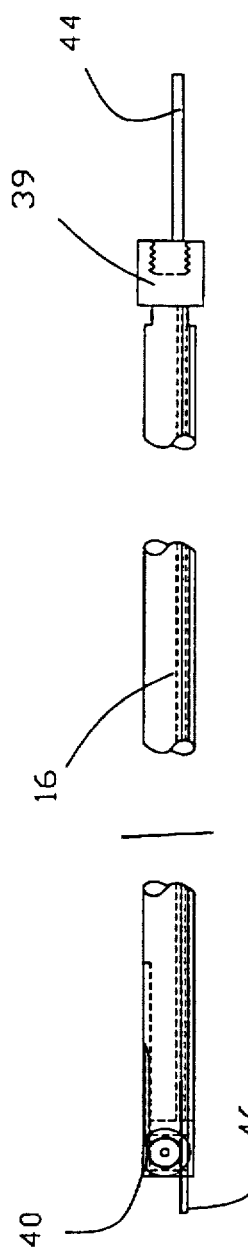
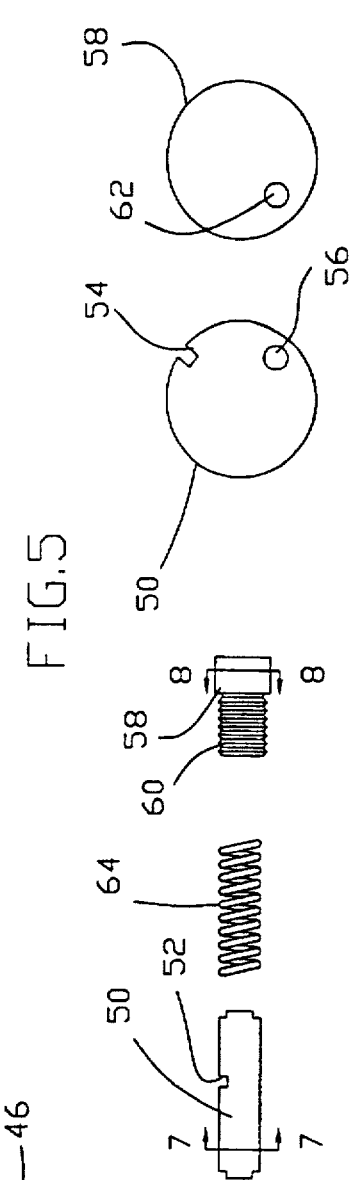
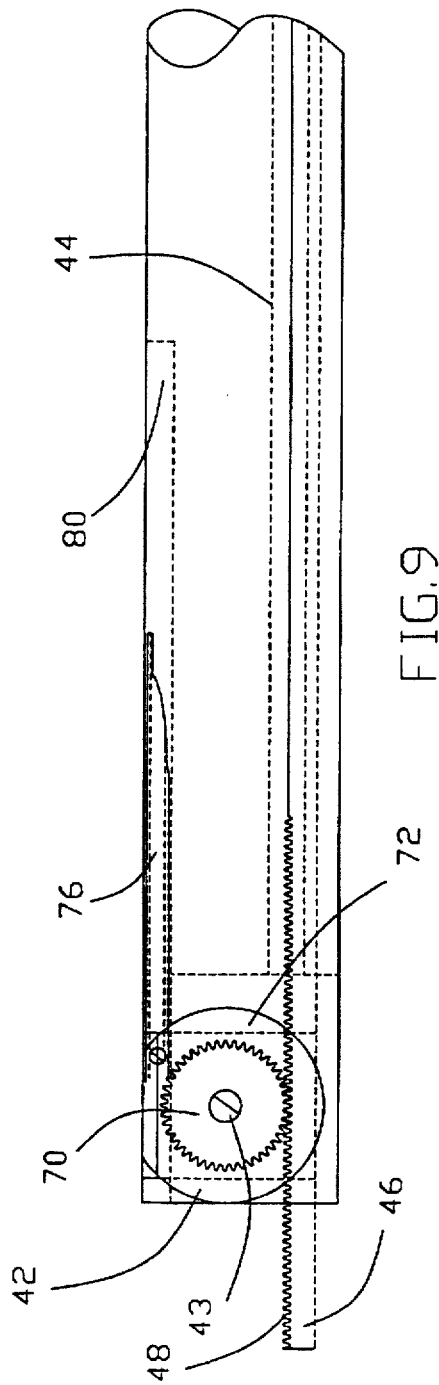

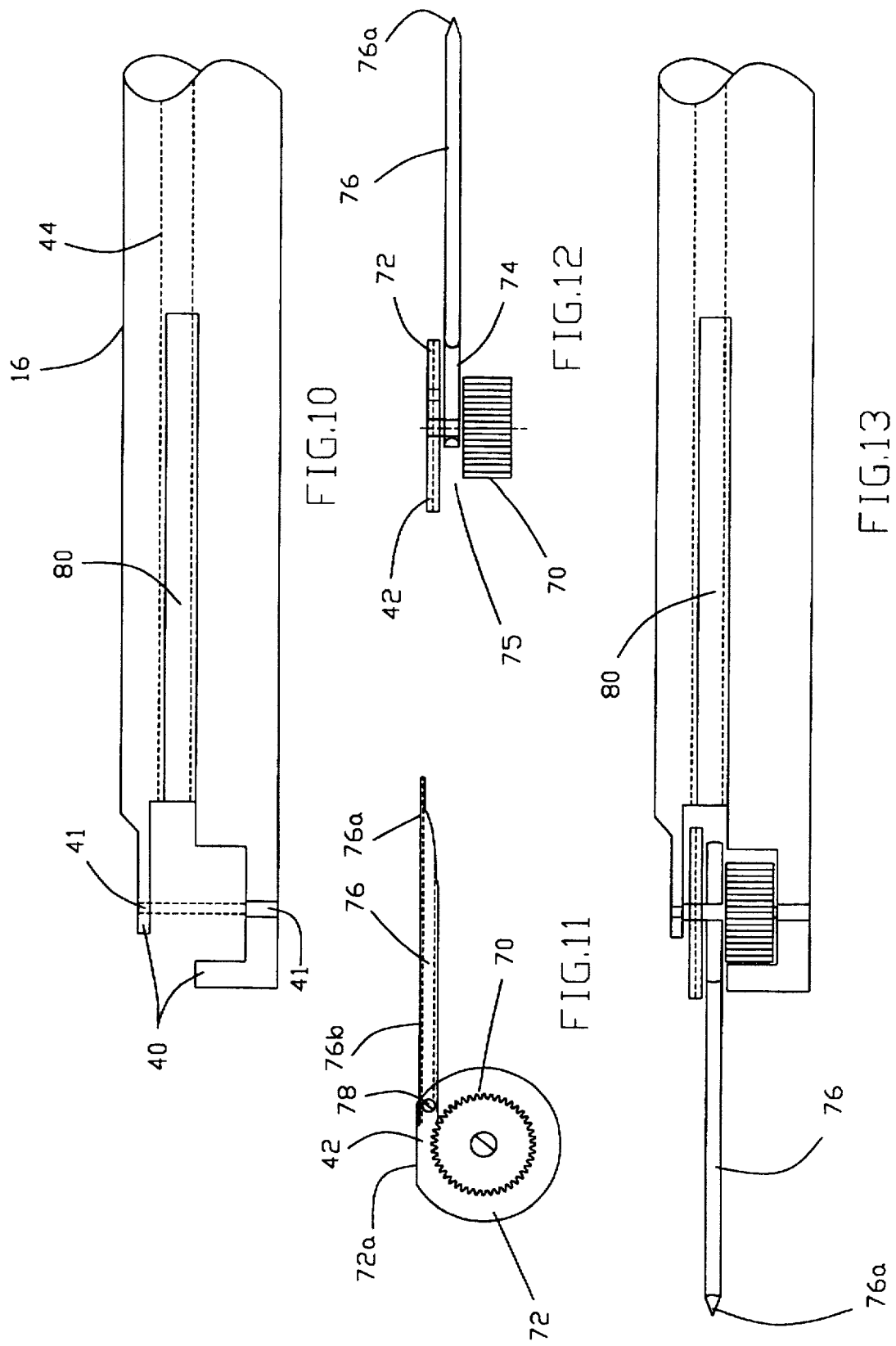

1

ELECTRODE DELIVERY INSTRUMENT

BACKGROUND OF THE INVENTION

1. Field of the Invention

The present invention relates generally to a surgical instrument, and, in particular, to a device for implanting electrodes into the muscular tissue of the abdomen to assist in the activation of the diaphragm.

2. Description of the Related Art

Cervical spinal cord injuries usually result in a loss of respiratory function. At present, treatment of this condition involves primarily mechanical, positive pressure ventilators, and, less frequently, phrenic nerve stimulation with cuff electrodes.

Positive pressure mechanical ventilation is the most common technique used to treat patients with respiratory insufficiency. Although these systems achieve adequate oxygenation, there are associated drawbacks, including decreased venous return, mobility, and the ability to speak.

Electric stimulation of the phrenic nerves has been shown to provide ventilatory support in chronic respiratory disorders including quadriplegia with respiratory paralysis and various central hypoventilation syndromes. Current techniques involve either a cervical or thoracic approach to place nerve cuff electrodes on the phrenic nerves. These systems allow speech more easily, artificial humidification is not needed, and the equipment is less intrusive. However, the possibility of phrenic nerve damage make these procedures less attractive, especially in patients with some degree of diaphragm function.

If, however, it were possible to approach the motor points and muscles of the diaphragm from the abdominal side, the open cervical or thoracic procedure can be avoided. By using a laproscopic procedure, which would require less time for implanting electrodes, recovery time is reduced, and the possibility of phrenic nerve damage is minimal, as the phrenic nerves are not manipulated when the procedure is performed through the abdomen.

The use of intramuscular electrodes as an alternative to the aforementioned procedures has been successful, as intramuscular electrodes have been proven to be safe and effective. As the electrodes can be placed in the diaphragm through the abdomen, diaphragm function can be restored, while the possibility of damage to the nerves is greatly reduced as the electrodes do not come into contact with the nerves.

However, several drawbacks may occur when using intramuscular electrodes. First, it is often difficult to accurately locate the points of phrenic nerve entry into the diaphragm. In addition, special care must be taken to keep the electrode insertion needle within the muscle without partially implanting the electrode into the thorax.

SUMMARY OF THE INVENTION

It is therefore an object of the present invention to provide a device which is able to implant intramuscular electrodes safely and accurately near the phrenic nerve motor points, thus activating the diaphragm muscle.

It is also an object of the present invention to provide a device which can implant intramuscular electrodes within the diaphragm muscle while reducing the risk of penetration of the thorax during the procedure.

Still further advantages of the present invention will become apparent to those of ordinary skill in the art upon reading and understanding the following detailed description of the preferred embodiment.

BRIEF DESCRIPTION OF THE DRAWINGS

FIG. 2 is a side elevational view of a handle of the instrument of the present invention;

FIG. 3 is a side elevational view of a second handle of the instrument of the present invention;

FIG. 4 is a front elevational view of the handle of FIG. 3;

FIG. 5 is a fragmentary view, partly in phantom, of the delivery shaft of the present invention;

FIG. 6 is a side elevational view of a section of the instrument of the present invention;

FIG. 7 is a cross-sectional view taken along lines 7—7 of FIG. 6;

FIG. 8 is a cross-sectional view taken along lines 8—8 of FIG. 6;

FIG. 9 is an enlarged side fragmentary view of the distal end of the delivery shaft of the present invention;

FIG. 10 is an enlarged top fragmentary view of the shaft shown in FIG. 9;

FIG. 11 is a side elevational view, partly in phantom, of the wheel assembly of the present invention;

FIG. 12 is a top elevational view of the wheel assembly of the present invention; and FIG. 13 is an enlarged top fragmentary view of the shaft shown in FIG. 9 in the activated position.

DETAILED DESCRIPTION OF THE PREFERRED EMBODIMENT

Figure 1:
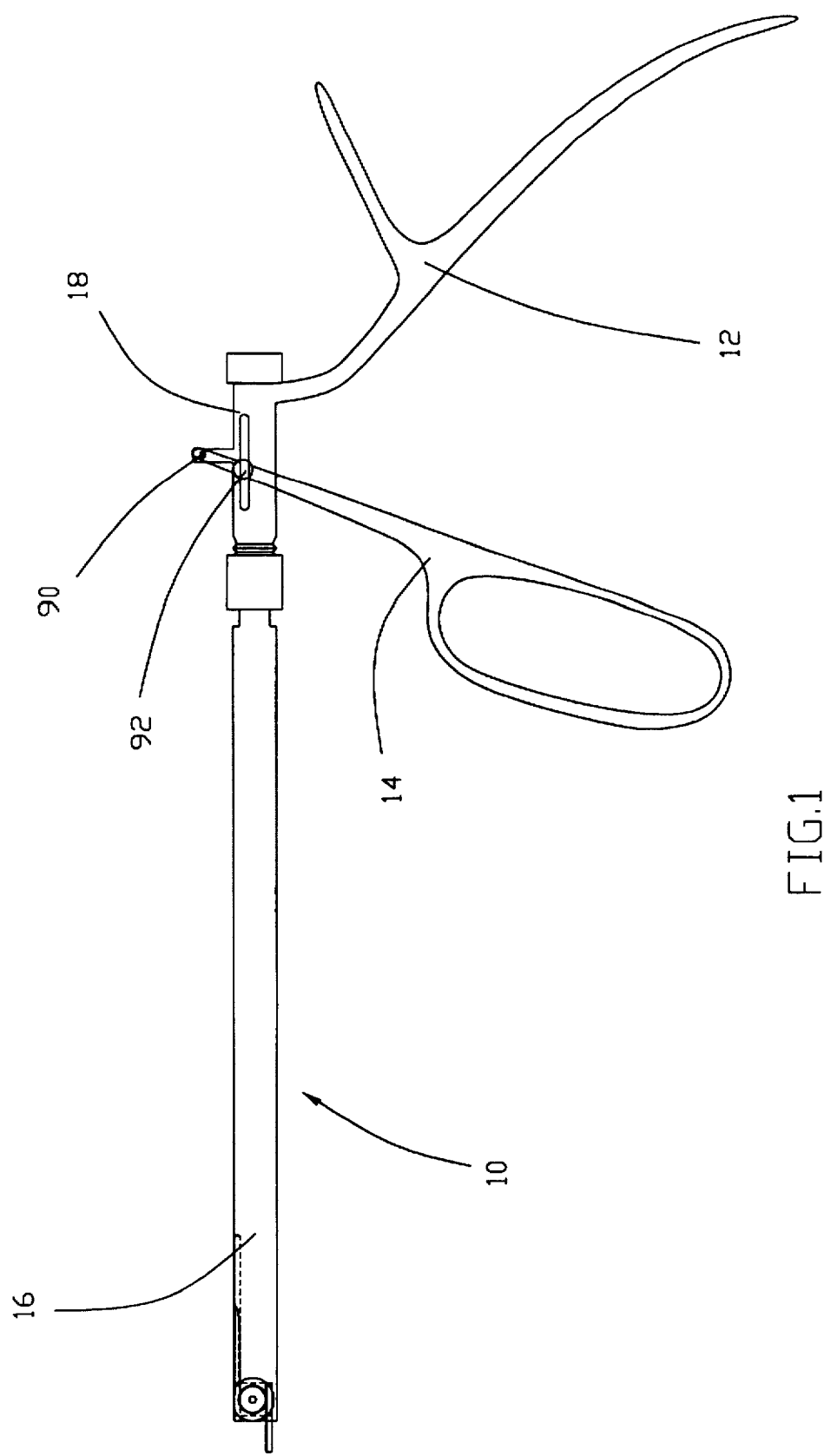
FIG. 1 is a side elevational view of an instrument in accordance with a preferred embodiment of the present invention.

Referring more particularly to the drawings there is shown therein an instrument, generally indicated at 10, which embodies the principles of the present invention. Instrument 10 contains a first handle 12 at its proximal end, a second handle 14, and a delivery shaft 16. Handle 12 includes tubular section 18 containing an externally threaded end 20, an internally threaded end 21, an upward extension 22 containing an aperture 24, and a through slot 26. Handle 12 also includes an elongate support 28 to facilitate the handling of the instrument by a user. Handle 14 includes a gripping ring 30 and a bifurcated upper section 32, with each arm of section 32 containing a pair of apertures 34 and 36. Delivery shaft 16 includes an internally threaded coupling 39 at one end and a bifurcated section 40, with each arm having an aperture 41, at the other end. A wheel assembly 42 is positioned within the bifurcations of section 40 by an axle 43. Located within shaft 16 is a delivery tube 44 and a drive rack 46. Rack 46 contains a toothed section 48 at its distal end.

An actuator 50 includes a groove 52 in its outer surface, along with a notch 54 in one end and through hole 56. An end cap 58 has an externally threaded end 60 in addition to a through hole 62. Finally, a compression spring 64 is located within the threaded end 60 of end cap 58.

FIGS. 11 and 12 more clearly illustrate wheel assembly 42 in greater detail. Assembly 42 includes a toothed gear 70, a disc-like member 72 having a flat section 72a, and a connecting section 74 between gear 70 and member 72. A channel 75 is formed by gear 70, member 72, and section 74, which can be best seen in FIG. 12. A hollow needle 76 having a pointed end 76a and a straight edge 76b is rigidly attached to member 72 by a screw 78 such that edge 76b is aligned with flat section 72a. Needle 76 is positioned within a channel 80 located within the top of drive shaft 16. Wheel assembly 42 is mounted on shaft 16 such that toothed gear 70 meshes with the toothed section 48 of drive rack 46.

Assembly of instrument 10 is accomplished in the following manner. Handle 12 is inserted between the forks of bifurcated section 32 of handle 14 and are pivotably coupled together by a pin 90 inserted through apertures 24 and 34, while actuator 50 is inserted into tubular section 18 of handle 12. Delivery shaft 16 is attached to handle 12 by threading coupling 39 onto end 20 while insuring that delivery tube 44 passes through hole 56 of actuator 50, and that rack 46 is connected into notch 54 of actuator 50. End 60 is then threadedly coupled to end 21 of handle 12, capturing spring 64 between actuator 50 and cap 58, while insuring that delivery tube 44 passes through hole 62. Finally, a pin 92 is located through apertures 36 of handle 14 within groove 52 of actuator 50.

The operation of instrument 10 will now be described. To activate the instrument, handle 14 is moved toward handle 12, which is kept stationary, and actuator 50, by virtue of the engagement of pin 92 within groove 52, is shifted toward end cap 58, compressing spring 64. This movement causes drive rack 46, which is also coupled to actuator 50, to shift rearwardly toward end cap 58. The rearward movement of drive rack 46 causes wheel assembly 42 to rotate in a counterclockwise direction as a result of the engagement of toothed section 48 of drive rock 46 with toothed gear 70. The rotation of wheel assembly 42 also causes needle 76 to rotate in the counterclockwise direction, as it is rigidly affixed to member 72 by screw 78, as can be seen in FIG. 13. In the present embodiment, needle 76 can be rotated through a range of motion from 0° (when it is at rest within channel 80) through an angle of approximately 220° in order to accommodate the most comfortable angle when approaching the desired implant site within the diaphragm muscle.

When the user of instrument 10 relaxes the grip on handles 12 and 14, compression spring 64 acts to return actuator 50 to its idle position, thus returning needle 76 to channel 80 within shaft 16.

The use of instrument 10 in a surgical procedure will now be described. An electrode to be implanted within the diaphragm muscle is inserted into needle 76. The lead wire of the electrode is routed within channel 75 and delivery tube 44, and extends from end cap 58. Preferably, a probe is employed to locate the phrenic nerve motor points to identify the optimal location for implanting. A laparoscope is also used to visualize the abdominal cavity and diaphragm muscle. Instrument 10 is then inserted through a small incision in the abdominal walls. When instrument 10 is inserted, needle 76 is kept in its idle position within channel 80, as no force is applied to handles 12 and 14. Upon entry into the abdomen, the position of needle 76 can be adjusted as desired to comfortably insert the electrode into the muscle, as the angle of needle 76 relates directly to the degree of compression of handles 12 and 14. When the desired implant site is located, tip 76a of needle 76 is inserted into the muscle, implanting the electrode approximately 1-2 millimeters beneath the abdominal surface of the diaphragm, with the stimulating tip of the electrode approximately midway between the thoracic and abdominal sides of the muscle.

The shape and design of needle 76 has been found to be a factor in accurate electrode placement. In the present embodiment, a 16 gauge needle with a 12° medical point was determined to be best suited for the task.

After the electrode has been implanted, the force on handles 12 and 14 is relaxed, allowing needle 76 to return to its idle position in channel 80 within shaft 16 such that instrument 10 can be easily removed from the abdomen through the incision. The lead wire of the electrode travels through delivery tube 44 until the lead wire is unloaded from the instrument.

As used herein and in the claims, such words as "distal", "proximal", "horizontal", "vertical", "top", "bottom", "forward", "upward", "rearward", "clockwise", "counterclockwise", and the like are used in conjunction with the drawings for purposes of clarity. It will be appreciated that instrument 10, in use, may be held in any appropriate orientation.

While the invention has been shown and described in terms of a preferred embodiment thereof, it will be understood that this invention is not limited to this particular embodiment and that many changes and modifications may be made without departing from the true spirit and scope of the invention as defined in the appended claims.

What is claimed is:

1. A device for implanting electrodes within the body of a mammal, comprising:
   an elongate frame having a first handle at a proximal end and a channel located within a distal end;
   a wheel assembly rotatably mounted at said distal end of said frame;
   a hollow needle, capable of carrying an electrode, rigidly affixed to said wheel assembly and positioned within said channel in said frame;
   a second handle movably coupled to said frame;
   and actuating means, coupled to said wheel assembly and said second handle;
   wherein when said second handle is shifted toward said first handle, said needle is rotated out of said channel within said frame such that said needle can implant an electrode within the body of a mammal.

2. The device of claim 1, wherein said second handle is biased away from said first handle.

3. The device of claim 2, wherein said biasing means comprises a compression spring.

4. The device of claim 1, wherein said needle is capable of rotation through a range of 0° within said channel to approximately 220°.

5. The device of claim 1, wherein said needle contains a 12° medical point.

6. The device of claim 1, wherein said elongate frame contains a tubular passageway within said frame extending from said distal end to said proximal end.

7. The device of claim 1, wherein said wheel assembly further comprises a toothed gear for mechanically coupling said wheel assembly to said actuating means.

8. The device of claim 7, wherein said actuating means includes a drive rack having a toothed portion in mechanical engagement with said toothed gear.

9. An instrument for implanting electrodes within the body of a mammal, comprising:
   an elongate hollow frame having a proximal end and a distal end, said proximal end including a first handle and said distal end including a channel located on the outer surface of said frame;
   a second handle pivotally coupled to said frame, said handle having an idle position away from said first handle;
   a wheel assembly rotatably attached at said distal end of said frame, said assembly including a toothed gear;

a hollow needle for holding an electrode, said needle being rigidly affixed to said wheel assembly and located within said channel of said frame when said second handle is at said idle position;

means for biasing said second handle to said idle position;

and actuating means mechanically coupling said second handle to said wheel assembly, said actuating means including a drive rack having a toothed portion in mechanical engagement with said toothed gear of said wheel assembly;

wherein when said second handle is shifted from said idle position, said needle is rotated out from said channel in said frame by said actuating means such that said needle is capable of implanting an electrode.

10. The instrument of claim 9, wherein said needle contains a 12° medical point.

11. The instrument of claim 9, wherein said needle is a 16 gauge needle.

12. The instrument of claim 9, wherein said frame contains a passageway within said frame extending from said proximal end to said distal end.

13. The instrument of claim 9, wherein said needle can be rotated from said channel by said actuating means when said second handle is in said idle position through an angle of approximately 220° when said second handle is adjacent said first handle.

* * * * *